(12) United States Patent
Karapasha et al.

(10) Patent No.: US 8,613,718 B2
(45) Date of Patent: Dec. 24, 2013

(54) TAMPON APPLICATOR

(75) Inventors: Nancy Karapasha, Monfort Heights, OH (US); Jutta Elisabeth Carolin Kreiter, Oberursel (DE); Dean Jeffrey Daniels, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 281 days.

(21) Appl. No.: 13/181,612

(22) Filed: Jul. 13, 2011

(65) Prior Publication Data

US 2011/0270150 A1 Nov. 3, 2011

Related U.S. Application Data

(63) Continuation of application No. 10/994,075, filed on Nov. 19, 2004, now Pat. No. 8,372,028.

(51) Int. Cl.
*A61F 13/32* (2006.01)

(52) U.S. Cl.
USPC .................. 604/18; 604/15; 604/13

(58) Field of Classification Search
USPC ...................................... 604/11–18
See application file for complete search history.

(56) References Cited

U.S. PATENT DOCUMENTS

| | | | |
|---|---|---|---|
| 2,489,502 A | 11/1949 | Ruth | |
| 2,879,769 A | 3/1959 | Gordon et al. | |
| 3,139,886 A | 7/1964 | Tellman et al. | |
| 3,148,680 A | 9/1964 | Roberts et al. | |
| 3,196,873 A | 7/1965 | Bletzinger | |
| 3,351,060 A | 11/1967 | Woslin | |
| 3,409,011 A | 11/1968 | Heinz Mittag | |
| 3,628,533 A | 12/1971 | Loyer | |
| 3,643,661 A | 2/1972 | Crockford | |
| 3,696,812 A | 10/1972 | Jaycox | |
| 3,699,962 A | 10/1972 | Hanke | |
| 3,765,416 A | 10/1973 | Werner et al. | |
| 3,807,399 A | 4/1974 | Morman et al. | |
| 3,831,605 A | 8/1974 | Fournier | |

(Continued)

FOREIGN PATENT DOCUMENTS

EP 0 349 222 A2 1/1990
GB 684290 A 12/1952

(Continued)

OTHER PUBLICATIONS

PCT Search Report, mailed Apr. 12, 2006, 6 pages.

(Continued)

*Primary Examiner* — Susan Su (74) *Attorney, Agent, or Firm* — Andrew J. Hagerty (57) ABSTRACT

A tampon applicator having an outer member adapted to house a tampon and receive an inner member. The outer member includes a fingergrip region having an indentation region that extends inwardly from the outer surface of the outer member. The indentation region has a depth dimension that is measured from the outer surface of the outer member to a lowest point of the indentation region. The indentation region comprises a first raised portion and a second raised portion, each of which having a height dimension that is measured from an individual raised portion's base to an individual raised portion's highest point, wherein the height dimension is less than the depth dimension. The first raised portion is a different size and a different shape as compared to the second raised portion.

10 Claims, 3 Drawing Sheets

(56) References Cited

U.S. PATENT DOCUMENTS

| | | | |
|---|---|---|---|
| 3,895,634 | A | 7/1975 | Berger et al. |
| 4,424,054 | A | 1/1984 | Conn et al. |
| 4,447,222 | A | 5/1984 | Sartinoranont |
| 4,479,791 | A | 10/1984 | Sprague |
| 4,536,178 | A * | 8/1985 | Lichstein et al. ............ 604/15 |
| 4,573,963 | A | 3/1986 | Sheldon |
| 4,573,964 | A | 3/1986 | Huffman |
| 4,891,042 | A | 1/1990 | Melvin |
| 4,911,687 | A | 3/1990 | Stewart |
| 4,921,474 | A | 5/1990 | Suzuki et al. |
| 5,080,659 | A | 1/1992 | Nakanishi |
| 5,290,501 | A | 3/1994 | Klesius |
| 5,330,421 | A | 7/1994 | Tarr |
| 5,346,468 | A | 9/1994 | Campion et al. |
| 5,348,534 | A | 9/1994 | Tomaszewski |
| 5,385,542 | A | 1/1995 | Rawlings |
| 5,389,067 | A | 2/1995 | Rejai |
| 5,395,309 | A | 3/1995 | Tanaka et al. |
| 5,497,542 | A | 3/1996 | Sengstock |
| 5,554,109 | A | 9/1996 | Frayman |
| 5,558,631 | A | 9/1996 | Campion |
| 5,599,293 | A | 2/1997 | Orenga |
| 5,643,196 | A | 7/1997 | Child et al. |
| 5,676,647 | A | 10/1997 | Cimber |
| 5,709,652 | A | 1/1998 | Hagerty |
| 5,738,646 | A | 4/1998 | Fox et al. |
| 5,931,803 | A | 8/1999 | Jackson |
| D415,565 | S | 10/1999 | Hayes et al. |
| 6,045,526 | A | 4/2000 | Jackson |
| 6,200,288 | B1 | 3/2001 | Heaton |
| 6,217,542 | B1 | 4/2001 | Stevens et al. |
| 6,248,089 | B1 | 6/2001 | Porat |
| 6,254,566 | B1 | 7/2001 | Buck |
| 6,264,626 | B1 | 7/2001 | Linares et al. |
| 6,302,861 | B2 | 10/2001 | Tweddell |
| 6,358,223 | B1 | 3/2002 | Mackay |
| 6,368,442 | B1 | 4/2002 | Linares |
| 6,413,247 | B1 | 7/2002 | Carlucci et al. |
| 6,416,488 | B1 | 7/2002 | Jackson |
| 6,423,025 | B1 | 7/2002 | Buzot |
| 6,432,076 | B1 | 8/2002 | Wada et al. |
| 6,450,986 | B1 | 9/2002 | Binner |
| 6,478,764 | B1 | 11/2002 | Suga |
| 6,511,452 | B1 | 1/2003 | Rejai |
| 6,610,025 | B2 | 8/2003 | Berg et al. |
| 6,673,032 | B2 | 1/2004 | Buzot |
| 6,730,057 | B2 | 5/2004 | Zhao et al. |
| D492,033 | S | 6/2004 | Jarmon et al. |
| 6,890,324 | B1 | 5/2005 | Jackson et al. |
| 7,044,928 | B2 | 5/2006 | Lemay et al. |
| 7,081,110 | B2 | 7/2006 | Karapasha |
| 7,704,242 | B2 | 4/2010 | Lemay et al. |
| 7,727,208 | B2 | 6/2010 | Lemay et al. |
| 2001/0014784 | A1 | 8/2001 | Tweddell |
| 2001/0014788 | A1 | 8/2001 | Morris |
| 2001/0049487 | A1 | 12/2001 | Buzot |
| 2002/0010413 | A1 | 1/2002 | Binner |
| 2002/0143287 | A1 | 10/2002 | Buzot |
| 2002/0165480 | A1 | 11/2002 | Jackson |
| 2002/0177801 | A1 | 11/2002 | Jackson |
| 2002/0183681 | A1 | 12/2002 | Bernard |
| 2002/0188283 | A1 | 12/2002 | Binner |
| 2002/0193726 | A1 | 12/2002 | Cimber |
| 2003/0236161 | A1 | 12/2003 | Fedyk et al. |
| 2003/0236485 | A1 | 12/2003 | Fedyk et al. |
| 2004/0010220 | A1 | 1/2004 | Miller |
| 2004/0064082 | A1 | 4/2004 | Lemay et al. |
| 2004/0199102 | A1 | 10/2004 | Lemay et al. |
| 2004/0243088 | A1 | 12/2004 | Lemay et al. |
| 2005/0038373 | A1 | 2/2005 | Avery, Jr. et al. |
| 2005/0113782 | A1 | 5/2005 | Carlin |
| 2005/0256483 | A1 | 11/2005 | Przepasniak et al. |
| 2007/0156081 | A1 | 7/2007 | Karapasha |
| 2007/0293809 | A1 | 12/2007 | Karapasha |
| 2008/0228128 | A1 * | 9/2008 | Karapasha et al. ............ 604/15 |

FOREIGN PATENT DOCUMENTS

| | | |
|---|---|---|
| GB | 2166656 B | 6/1988 |
| WO | WO-9904741 A1 | 2/1999 |
| ZA | 777411 | 12/1977 |

OTHER PUBLICATIONS

PCT Search Report, mailed Nov. 17, 2004, 5 pages.
U.S. Appl. No. 10/621,709, filed Jul. 17, 2003: Notice of Allowance, mail date Apr. 11, 2006, 12 pages.
U.S. Appl. No. 10/621,709, filed Jul. 17, 2003: Office Action, mail date Aug. 22, 2005, 7 pages.
U.S. Appl. No. 10/621,709, filed Jul. 17, 2003: Office Action, mail date May 10, 2005, 6 pages.
U.S. Appl. No. 11/472,738, filed Jun. 22, 2006: Office Action, mail date Oct. 22, 2009, 17 pages.
U.S. Appl. No. 11/472,738, filed Jun. 22, 2006: Office Action, mail date May 8, 2009, 15 pages.
U.S. Appl. No. 11/472,738, filed Jun. 22, 2006: Office Action, mail date Dec. 26, 2008, 16 pages.
U.S. Appl. No. 11/472,738, filed Jun. 22, 2006: Office Action, mail date Apr. 16, 2008, 14 pages.
U.S. Appl. No. 11/895,126, filed Aug. 23, 2007: Office Action, mail date Dec. 23, 2009, 15 pages.
U.S. Appl. No. 11/895,126, filed Aug. 23, 2007: Office Action, mail date May 6, 2009, 14 pages.
U.S. Appl. No. 11/895,126, filed Aug. 23, 2007: Office Action, mail date Nov. 24, 2008, 15 pages.
U.S. Appl. No. 10/994,076, filed Nov. 11, 2004: Examiner's Answer, mail date Jul. 8, 2010, 14 pages.
U.S. Appl. No. 10/994,076, filed Nov. 11, 2004: Office Action, mail date Sep. 29, 2009, 13 pages.
U.S. Appl. No. 10/994,076, filed Nov. 11, 2004: Office Action, mail date Jun. 18, 2009, 13 pages.
U.S. Appl. No. 10/994,076, filed Nov. 11, 2004: Office Action, mail date Jan. 8, 2008, 11 pages.
U.S. Appl. No. 10/994,076, filed Nov. 11, 2004: Examiner's Answer, mail date Sep. 13, 2007, 11 pages.
U.S. Appl. No. 10/994,076, filed Nov. 11, 2004: Office Action, mail date Dec. 8, 2006, 9 pages.
U.S. Appl. No. 10/994,076, filed Nov. 11, 2004: Office Action, mail date Jul. 18, 2006, 9 pages.
U.S. Appl. No. 10/994,076, filed Nov. 11, 2004: Office Action, mail date Jan. 31, 2006, 9 pages.

* cited by examiner

TAMPON APPLICATOR

CROSS-REFERENCE TO RELATED APPLICATION

This application is a continuation of U.S. application Ser. No. 10/994,075, filed on Nov. 19, 2004 now U.S. Pat. No. 8,372,028.

FIELD OF INVENTION

This invention relates to a tampon applicator, particularly, to a tampon applicator in which the inner tube is moved forward to eject the tampon from the tampon applicator.

BACKGROUND OF THE INVENTION

Tampon applicators have been used for inserting a tampon into a vaginal cavity to prevent leakage of menstrual fluids or other fluids. In the field of tampon applicators, "push" type tampon applicators are well known. These applicators generally comprise, in a simple form, a pair of coaxial hollow cylinders or tubes. The larger outer tube serves as a vaginal insertion tube and houses a tampon. The inner tube serves as a plunger which ejects the tampon from the outer tube.

It has been recognized that tampon applicators of the type described above have certain deficiencies which can be readily apparent to many users of such devices. In general, the user removes the tampon applicator from the package. During removal, however, the outer member may be inadvertently removed from the inner member because there is not a lock formed between the outer member and the inner member.

Another deficiency with the tampon applicator occurs during removal of the tampon applicator from the vaginal cavity. After insertion of the tampon applicator into the vaginal cavity, when an axial force is applied along the longitudinal axis to the inner member, the inner member slides toward the insertion end of the outer member and bears against the rear end of the tampon expelling the tampon from the tampon applicator. Unfortunately, the user may plunge the inner member too far inside the outer member resulting in the insertion of the inner member into the body cavity. Because the inner member is inserted into the body cavity, during removal of the tampon applicator from the body cavity and there is not a lock to prevent the separation from the inner member from the outer member, the body tissues will hold onto the inner member with the vaginal tissues and body pressure. Because the body tissues hold onto the inner member which is now separated from the outer member, the tampon applicator exits the body cavity without the inner member, i.e., leaving the inner member behind.

To solve the above problem of the outer member separating from the inner member, it would be beneficial to provide a tampon applicator which provides a locking mechanism to prevent the inner member from separating from the outer member.

SUMMARY OF THE INVENTION

The present invention encompasses a tampon comprising an outer member adapted to house a tampon and receive an inner member. The outer member comprises an insertion end, a gripper end, and an interior surface. The inner member comprises a first end and a second end. The first end is spaced a first distance from a first longitudinal protrusion. The second end is spaced a second distance from a second longitudinal protrusion. The first distance is less than about 7 mms. The second distance is less than about 7 mms. In one embodiment, the first distance is at less than about 3 mms and the second distance is less than about 3 mms.

In yet another embodiment of the present invention, the outer member further comprises an indentation region. The indentation region has a first end and a second end. The gripper end is spaced a distance to the first end of the indentation region. The indentation region and the first longitudinal protrusion interlock to resist withdrawal of the inner member from the outer member. In yet another alternative embodiment, the indentation region and the second longitudinal protrusion interlock to resist withdrawal of the inner member from the outer member.

In yet another aspect of the present invention, an applicator device is capable of housing an insertable element having an outer member having an insertion end and a gripper end. The inner member may have a first end and a second end. The first end is spaced a first distance from a first raised portion wherein the first raised portion extends radially outward, away from the longitudinal axis of the inner member. The second end is spaced a second distance from a second raised portion, wherein the second raised portion extends radially outward, away from the longitudinal axis of the inner member. Moreover, the outer member may comprise an indentation region. The indentation region has a first end and a second end. The gripper end is spaced a distance to the first end of the indentation region. In one embodiment, the indentation region and the first raised portion interlock to resist withdrawal of the inner member from the outer member. In yet another embodiment, the indentation region and the second raised portion interlock to resist withdrawal of the inner member from the outer member.

In yet another alternative embodiment, a tampon applicator comprises an outer member adapted to house a tampon and receive an inner member. The inner member comprises a first end and a second end. The second end is spaced a distance from a longitudinal protrusion.

In yet another alternative embodiment, a tampon applicator comprises an outer member adapted to house a tampon and receive an inner member. The inner member comprises a first end and a second end. The first end is housed within the outer member. The second end is exposed. The second end is spaced a distance from a longitudinal protrusion.

DETAILED DESCRIPTION OF THE INVENTION

Section A will provide terms which will assist the reader in best understanding the features of the invention but not to introduce limitations in the terms inconsistent with the context in which they are used in this specification. These definitions are not intended to be limiting. Section B will discuss the tampon applicator of the present invention. Section C will discuss the tampon applicator materials.

A. Terms

As used herein, the term "tampon" refers to any type of absorbent structure that can be inserted into the vaginal cavity or other body cavities for the absorption of fluid therefrom or for the delivery of active materials, such as medicaments or moisture. A tampon can be straight or non-linear in shape, such as curved along the longitudinal axis.

Generally, there are two types of tampons. The first type of tampon is a self-sustaining tampon. Tampons are generally "self-sustaining" in that they will tend to retain their general shape and size before use. A typical self-sustaining tampon is 35-60 millimeters long, the length measured from the top of the tampon to the base of the tampon along a longitudinal axis. The measurement to the base of the tampon does not include any overwrap, secondary absorbent member, or withdrawal cord which extends beyond the tampon's main absorbent material. A typical self-sustaining tampon is 5-20 millimeters wide corresponding to the largest cylindrical cross section. The width can vary along the length of the self-sustaining tampon.

The second type of tampon is an easily "deformable, fluid-permeable bag tampon". The deformable, fluid-permeable bag tampon consists of pieces such as absorbent chips, spheres, or fibers such that the fluid permeable bag tampon is readily deformable with a force of less than about 3 psi.

As used herein, the terms "vaginal cavity" and "within the vagina" refer to the internal genitalia of the human female in the pudendal region of the body.

The term "interlock," as used herein, is meant the interference fit between the indentation region of the outer member and the first longitudinal protrusion and/or the second longitudinal protrusion. The interference fit between the longitudinal protrusions and the indentation region is about 0.5-0.6 mm. It is preferred that the interference fit be adequate to provide a disassembly force of at least 100 grams, more preferably greater than 300 grams measured by a Dillon Force Gauge.

The term "spaced from," as used herein, is meant the distance from the absolute end of the outer or inner member to the first portion of the longitudinal protrusion or indentation region.

The term "diameter," as used herein, means a chord passing through the center of a figure or body; the length of a straight line through the center of an object.

The term "exposed," as used in herein, means any portion of the inner member which is not contained in the outer member before expulsion of the tampon from the tampon applicator.

B. Tampon Applicator of the Present Invention

Figure 1:
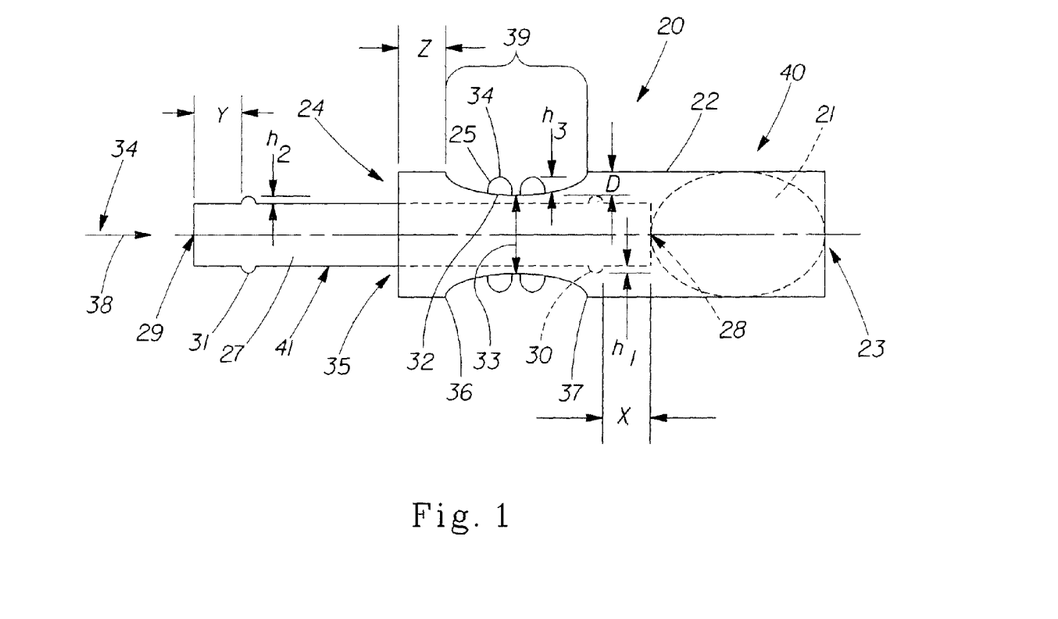
FIG. 1 is a side view of a tampon applicator of the present invention.

Referring to FIG. 1, the tampon applicator 20 includes an outer member 22 and an inner member 27. The outer member 22 retains tampon 21. Moreover, the outer member 22 comprises an outer surface 40, an insertion end 23 and a gripper end 24 opposed to the insertion end 23. The insertion end 23 is a portion of the outer member 22 in which the tampon applicator 20 is first inserted into the vaginal cavity and it is the end from the tampon 21 is expelled. During insertion of the tampon applicator 20 into the body of a wearer, the gripper end 24 can be used to hold the outer member 22 during insertion. The insertion end 23 of outer member 22 can include a plurality of petals (not shown). Preferably, the plurality of petals (not shown) are collectively shaped to form a dome or any shape in general which facilitates insertion.

In addition, the outer member 22 can contain a fingergrip region 39 disposed about outer surface 40. The fingergrip region 39 comprises an indentation region 33. The indentation region 33 is located adjacent to the gripper end 24 of the outer member 22. The indentation region 33 has a first end 36 and a second end 37. The indentation region 33 projects into the hollow interior portion 35 of the outer member 22. The first end 36 of the indentation region 33 is spaced a distance z from the gripper end 24.

The inner member 27 is dimensioned to slidably move within the hollow interior portion 35 of the outer member 22, with minimal clearance therebetween. Inner member 27 is adapted to slideably engage the outer member 22 and to contact tampon 21 to expel the tampon 21 through the insertion end 23. The inner member 27 has a first end 28 and a second end 29 opposed to the first end 28. The first end 28 is the most proximal end of the inner member 27 to the insertion end 23 of the outer member 22 along the longitudinal axis 34. The first end 28 provides the necessary axial force 38 to expel the tampon 21. The second end 29 is the portion of the inner member 27 in which an axial force 38 along the longitudinal axis 34 is applied to expel the tampon 21 through the insertion end 23 of the outer member 22.

The inner member 27 can have longitudinal protrusion(s) 30, 31. The longitudinal protrusion(s) 30, 31 project beyond the outer surface 41 of the inner member 27. The inner member 27 has a longitudinal protrusion 31 spaced a distance y from the second end 29 of the inner member 27. In addition, the inner member 27 can have an additional longitudinal protrusion 30 spaced a distance x from the first end 28 of the inner member 27.

To use the tampon applicator 20 of the present invention, the user will typically hold the indentation region 33 located adjacent to the gripper end 24 of the outer member 22 with the wearer's thumb and index finger. While holding the indentation region 33, the user can insert the outer member 22 of the tampon applicator 20 into the vaginal cavity and apply an axial force 38 sufficient enough to push the inner member 27 into the outer member 22. When the tampon 21 begins to be pushed out of the insertion end 23 of the outer member 22 with the axial force 38 applied along the longitudinal axis 34, petals (not shown), if included, begin to open.

In addition to delivering menstrual tampons into the vaginal cavity, it should be noted that the tampon applicator of the present invention can be used to deliver any other type of absorbent or nonabsorbent object to any suitable cavity. For example, the tampon applicator of the present invention could be used to insert incontinence inserts. An "incontinence insert," as used herein, refers to devices specifically designed, configured, and/or adapted for placement into a vagina in order to reduce the occurrence and/or severity of female urinary incontinence. While incontinence inserts are typically made of non-absorbent materials, at least partially absorbent materials may also be used. However, because there is no intent to absorb bodily fluids, and because the incontinence inserts are adapted and configured to provide structural support to the musculature and body tissues located near the urethra-vaginal myfascial area, incontinence inserts are readily distinguishable from tampons.

Below will provide more detail of each component of the tampon applicator of the present invention.

i. Outer Member

Referring to FIG. 1, typically, the outer member 22 can be used to handle or grip the tampon applicator 20 during the insertion into the vaginal cavity. The outer member 22 is external to the inner member 27. The outer member 22 has a hollow interior 35, an insertion end 23, and a gripper end 24 opposed to the insertion end 23. The insertion end 23 is a portion of the outer member 22 in which the tampon applicator 20 is first inserted into the vaginal cavity and it is the end from the tampon 21 is expelled. The gripper end 24 is opposed to the insertion end 23. At least a portion of the hollow interior 35 of the outer member 22 can engage with at least a portion of the inner member 27.

The outer member 22 has an outer surface 40 and a fingergrip region 39 disposed about the outer surface 40. The fingergrip region 39 comprises an indention region 33. The indentation region 33 has a first end 36 and a second end 37. The indentation region 33 projects into the hollow interior 35 and the first end 36 is spaced a distance z from the gripper end 24 of the outer member 22. When the indentation region 33 interlocks with the longitudinal protrusion(s) 30, 31 located on the inner member 27, a secure hold is created between the outer member 22 and the inner member 27. Interlocking could be provided by an interference fit between the longitudinal protrusions 30, 31 and the indentation region 33 which would cause longitudinal protrusion 30, 31 to interlock therewith. The indentation region 33 interlocks with the longitudinal protrusions 30, 31 to resist inadvertent separation from the inner member 27.

The indentation region has a depth dimension D as measured from the outer surface 40 of the outer member 22 to the lowest point of the indention region 33. In some embodiments, the depth dimension D may range from about 1 mm to about 10 mm as measured from the outer surface 40 of the outer member 22 to the lowest point of the indention region 33. In some embodiments, the depth dimension D may range from about 2 mm to about 5 mm as measured from the outer surface 40 of the inner member 22 to the lowest point of the indention region 33. In other embodiments, the depth dimension D may range from about 0.25 mm to about 0.381 mm as measured from the outer surface 40 of the inner member 20 to the lowest point of the indention region 33.

Referring again to FIG. 1, the indentation region 33 can provide for secure handling of the outer member 22. Furthermore, it is preferable that the indentation region 33 be of sufficient dimension to substantially provide a comfortable grip for the user. As used in the specification, the term "user's grip" means any way of holding the tampon applicator 20 in a hand, e.g., between a thumb and a finger. The indentation region 33 need not necessarily extend completely around the perimeter of the outer member 22. For example, a space can be provided for a decorative marking or a Trademark character.

The indentation region 33 may have a raised surface 25 above or below the plane of the outer member 22. The raised portions 25 may range from 1 to 200 depending on the size of the outer member 22 and the indentation region 33. The raised surface 25 has a height dimension $h_3$ as measured from the base 32 to the highest point 34 of the individual raised portion. In some embodiments, the height dimension $h_3$ ranges from about 0.1 mm to about 10 mm as measured from the base 32 to the highest point 34 of the individual raised portion. In some embodiments, the height dimension $h_3$ ranges from about 0.2 mm to about 5 mm as measured from the base 32 to the highest point 34 of the individual raised portion. In other embodiments, the height dimension $h_3$ ranges from about 0.5 mm to about 2.5 mm as measured from the base 32 to the highest point 34 of the individual raised portion.

The individual raised portions 25 may be formed to have essentially identical size and shape as compared to other individual raised portions 25. Alternatively, the individual raised portions 25 may be formed to have various sizes and shapes as compared to other individual raised portions 25. The raised portions 25 may be arranged randomly or in a pattern. For example, the raised portions 25 can be arranged to form any three-dimensional geometric pattern known including but not limited to flowers, ovals, circles, rectangles, trapezoids, triangles, cones, alphabet letters, and mixtures thereof. Alternatively, these raised portions 25 may be randomly arranged so that the multiplicity of the molded or attached dimples may comprise merely a surface roughness in no apparent pattern. In addition, raised portions 25 may be arranged such that the areas between the raised portions 25 may form any geometric pattern known including but not limited to flowers, ovals, circles, rectangles, trapezoids, triangles, cones, alphabet letters, and mixtures thereof.

The indentation region 33 can be any number, shape, or size. Any number of indentation regions 33 may be utilized. The indentation region 33 can be circular, square, rectangular, triangular, arced, curved, or any other conceivable shape possible as long as the indentation region 33 is able to interlock with the longitudinal protrusion(s) 30, 31. Moreover, the indentation region 33 can be any size as long as the indentation region 33 is able to interlock with longitudinal protrusion 30, 31.

The perimeter of the indentation region 33 can take essentially any desired shape, including oval, circular, and various other geometric forms. The indentation region 33 can be defined by outward protrusions or raised surfaces 25, created by impressing or compressing the surfaces. The indentation region 33 is substantially circularly shaped, but it can also take on more angular formations such as squared. The surface of the indentation region 33 can be any kind of surface known in the art. This surface can provide a desired frictional resistance for the fingers during the insertion of the tampon applicator 20 into the body.

The indentation region 33 can be joined to the outer member 22 or formed in the outer member 22 in any way known in the art. The indentation region 33 can also be monolithic with the outer member 22, for example, by molding the indentation region 33 and the outer member 27 as one piece. In one non-limiting example, the indentation region 33 can be joined to the outer member 22 by friction fitting that snaps parts together, gluing, and/or melting.

Indentation region 33 is typically formed inherently by the embossing process. While any conventional embossing technique can be utilized, a preferred method is to support the outer member on a central mandrel having circumferential ridges in its surface, and contact the surface of the outer member with a set of dies having indentations corresponding in shape to the ridges on the mandrel. It is also preferred that heat be employed during the embossing process to enhance the formability of the paper.

The manufacturer of the tampon applicator 20 can vary the size of the outer member 22. The inner diameter of the outer member 22 is typically just greater than the diameter of the tampon 21 that is to be accommodated therein. The size of the outer member 22 can be determined primarily by the dimensions of the tampon 21. Specifically, the diameter of the outer member 22 can be varied to accommodate different absorbency tampons 21. Generally, the outer member 22 can include an inner diameter of from about 6 millimeters to about 20 millimeters and a wall thickness of from about 0.4 millimeter to about 2.0 millimeters. Generally, the inner diameter of the outer member 22 should be suitably greater than the diameter of the tampon 21 to prevent the outer member 22 from interfering with the expulsion of the tampon 21 from the outer member 22. Moreover, the inner diameter of the outer member 22 can have varying diameters and shapes to conform to the profiled shape of the enclosed tampon 21.

Also, the manufacturer of the tampon applicator 20 can vary the length of the outer member 22. Generally, the outer member 22 should be of a sufficient length to house at least a portion of the tampon 21 prior to the expulsion of the tampon 21 from the tampon applicator 20 into the vaginal cavity.

In addition, the manufacturer of the tampon applicator 20 can vary the shape of the outer member 22. It is further noted herein that the shape of the outer member 22 can vary as long as a portion of the inner member 27 can be slideable within the outer member 22. Moreover, the outer member 22 is in no way limited by the shape that it can assume except that the shape should not hinder directional expulsion of the tampon 21. One skilled in the art can imagine that the outer member 22 might be cylindrical or curved like a banana or any other suitable shape as long as any such shape would work effectively to expel tampon 21 from the tampon applicator 20, and comfortably insert the tampon 21 into the vaginal cavity. The outer member 22 can be of any suitable cross-sectional shape. For example, suitable cross-sectional shapes can include, but are not limited to, circular, oval, flattened circular, elliptical, and any combination thereof.

ii. Inner Member

Referring to FIG. 1, the inner member 27 has a first end 28 and a second end 29 opposed to the first end 28. The first end 28 is the most proximal end of the inner member 27 to the insertion end 23 of the outer member 22 along the longitudinal axis 34. The first end 28 provides the necessary force to expel the tampon 21. The second end 29 is the portion of the inner member 27 in which an axial force 38 along the longitudinal axis 34 is applied to expel the tampon 21 through the insertion end 23 of the outer member 22. Longitudinal protrusion 30 is located a distance x spaced from the first end 28. Likewise, longitudinal protrusion 31 is located a distance y spaced from the second end 29 of the inner member 27. Longitudinal protrusion 30, 31 are described in more detail below.

The manufacturer of the tampon applicator 20 can vary the shape of the inner member 27. One skilled in the art can imagine other shapes of the inner member 27, for example, cylindrical or curved like a banana or any other suitable shape possible. The inner member 27 can be of any suitable cross-sectional shape including, but are not limited to, circular, oval, flattened circular, elliptical, and any combinations thereof.

The size of the inner member 27 can be determined primarily by the dimensions of outer member 22. The diameter of the inner member 27 is typically just smaller than the diameter of the outer member 22. Specifically, the diameter of the inner member 27 can be varied to accommodate the diameters of different outer members 22. For example, higher absorbency tampons can have larger diameters resulting in the outer member 22 diameter having a larger diameter to house the higher absorbent tampon. Because the outer member 22 diameter is larger, the inner member 27 diameter will also be larger. In addition, the inner member 27 diameter can have varying diameters and shapes to conform to the profiled shape of the outer member 22.

The length of the inner member 27 can also vary. Generally, the inner member 27 should be of a sufficient length to properly expel tampon 21 from the tampon applicator 20. For example, the length of the inner member 27 can be from about 43 millimeters to about 90 millimeters.

Longitudinal Protrusion(s)

Referring to FIG. 1, inner member 27 comprises longitudinal protrusions 30, 31, which interlock with the indentation region 33 to resist inadvertent separation of the inner member 27 from the outer member 22. The longitudinal protrusions 30, 31 can be adapted to interlock with the indentation region 33 which projects into the hollow interior portion 35 of outer member 22. Thus, the engagement of the longitudinal protrusions 30, 31 and the indentation region 33 serves to secure the outer member 22 and the inner member 27 in place.

a. Inner Member Having One Longitudinal Protrusion

In one embodiment, a longitudinal protrusion 31 may be placed on the inner member 27. Referring to FIG. 1, the inner member 27 has a longitudinal protrusion 31 spaced a distance y from the second 29 of the inner member 27. When the longitudinal protrusion 31 engages with the indentation region 33, the longitudinal protrusion 31 acts as a stop and a signal to the user that the contents of the tampon 21 have been fully expelled. In addition, longitudinal protrusion 31 provides resistance to the separation of the inner member 27 from the outer member 24. By increasing the resistance between the outer member 24 and the inner member 27, the separation of the outer member 24 and the inner member 27, and as a result, the risk of inserting the inner member 27 into the vagina itself and possibly being left behind in the body cavity are minimized. Additionally, the longitudinal protrusion 31 provides a user with greater resistance thereat, increasing her confidence in using the tampon applicator 20.

The longitudinal protrusion 31 is located at a distance y from the second end 29 of inner member 27. Generally, the longitudinal protrusion 31 of the inner member 27 can be spaced from about 1 millimeters to about 7 millimeters along the longitudinal axis 34. The distance y can be spaced preferably from about 2 mm to about 5 mm, more preferably from about 2 mm to about 4 mm.

b. Inner Member Having Two Longitudinal Protrusions

In another embodiment, in addition to the longitudinal protrusion 31 discussed in the afore-mentioned section, the inner member 27 can have an additional longitudinal protrusion 30 spaced a distance x from the first end 28 of the inner member 27. Ultimately, longitudinal protrusion 30 prevents the inner member 27 from too easily being separated from the outer member 22 should the tampon applicator 20 be mishandled before the use thereof. Specifically, when the longitudinal protrusion 30 interlocks with the indentation region 33, the inner member 27 is prevented from being inadvertently separated from the outer member 22.

The longitudinal protrusion 30 is located at a distance x from the first end 28 of inner member 27. Generally, the longitudinal protrusion 30 of the outer member 22 can be spaced from about 1 millimeters to about 7 millimeters along the longitudinal axis 34. The distance can be spaced preferably from about 2 mm to about 5 mm, more preferably from about 2 mm to about 4 mm.

c. Longitudinal Protrusions

Figure 2:
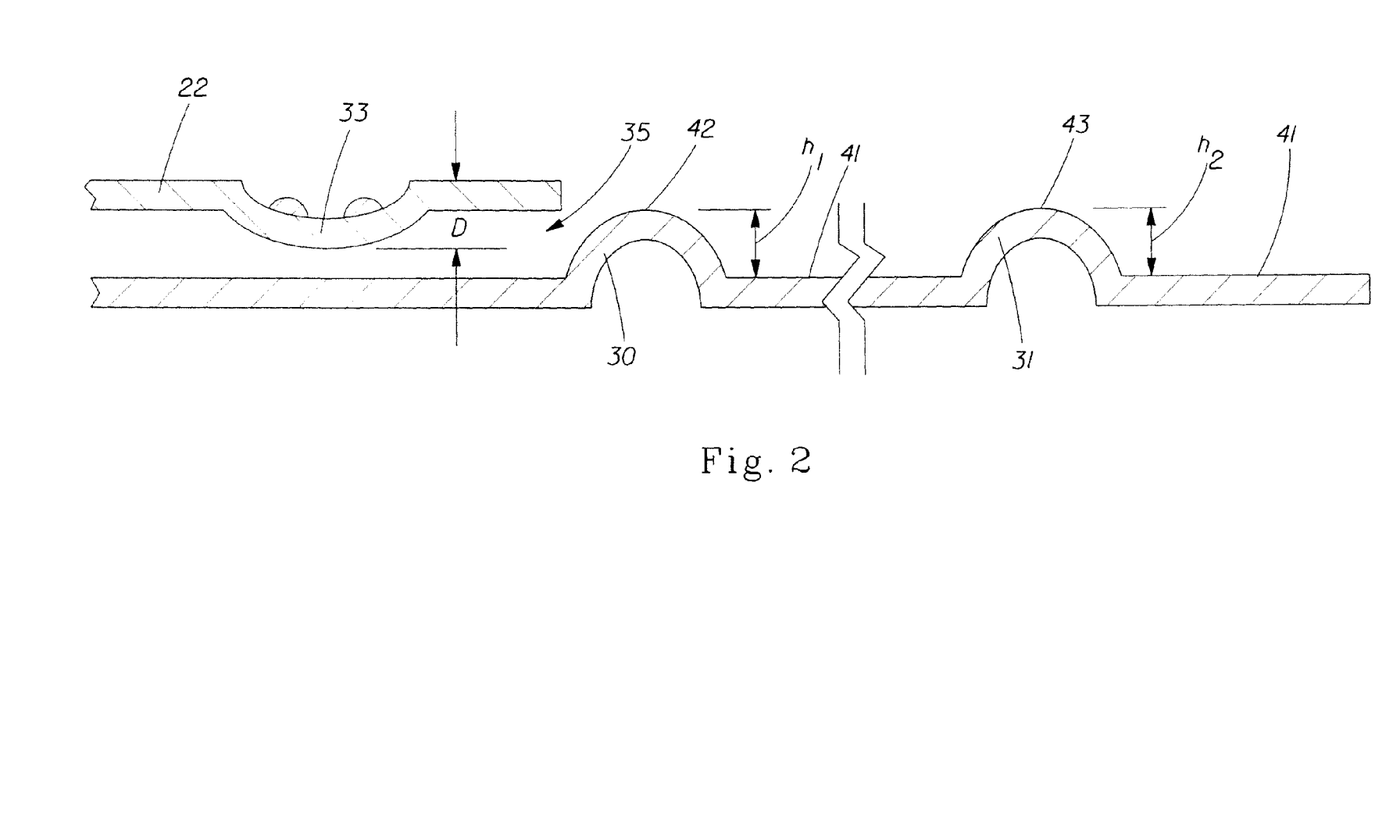
FIG. 2 is a cross-sectional view of the tampon applicator illustrative of the present invention.

Referring to FIG. 2, this section will provide more detail of the longitudinal protrusions 30, 31. The longitudinal protrusions 30, 31 are adapted to engage with the indentation region 33 with a depth dimension D located on the hollow interior portion 35 of the outer member 22.

The longitudinal protrusion 30 has a height dimension $h_1$ as measured from the outer surface 41 of the inner member 27 to the highest point 42 of the longitudinal protrusion 30. The height dimension $h_1$ of the longitudinal protrusion 30 is preferably at least about 0.5 mm and more preferably at least about 0.6 mm.

The longitudinal protrusion 31 has a height dimension $h_2$ as measured from the outer surface 41 of the inner member 27 to the highest point 43 of the longitudinal protrusion 31. The height of the longitudinal protrusion $h_2$ is preferably at least about 0.25 mm, and more preferably at least about 0.381 mm and more preferably at least about 0.6 mm.

Figure 3:
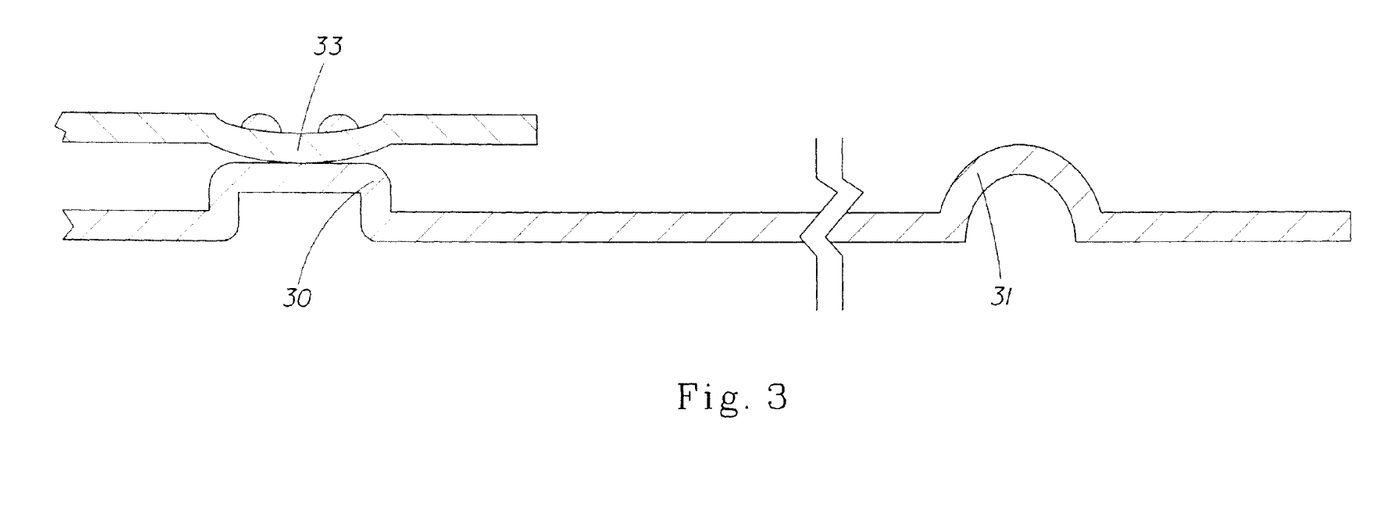
FIG. 3 is a cross-sectional view of the tampon applicator illustrative of the present invention.

Interlocking is assisted by the interference fit between the longitudinal protrusions 30, 31 and the indentation region 33. The interference fit between the longitudinal protrusions 30, 31 and the indentation region 33 is about 1 mm or preferred at about 3 mm. Referring to FIG. 3, an example of the use of a longitudinal protrusion 30 interlocking with an indentation region 33 is illustrated. Longitudinal protrusion 31 can also interlock with indentation region 33 in the same way as illustrated in FIG. 3. It is preferred that the interference fit be adequate to provide a disassembly force of at least 100 grams, more preferably greater than 300 grams as measured by a Dillon Force Gauge.

Referring again to FIG. 1, this interference can be accomplished in any numbers of ways. Preferably, the interference is accomplished by configuring the longitudinal protrusions 30,31 such that at least a portion of the longitudinal protrusions 30,31 must project beyond an area defined by the inner dimensions of the inner member 27. Preferably, the outer diameter of the inner member 27 is slightly greater than the inner diameter of the indentation region 33. While the inner member 27 is being pushed inside of the hollow interior portion 35 of outer member 22, the longitudinal protrusions 30,31 project beyond the outer surface 41 of the inner member 27 to interfere with the indentation region 33 on the hollow interior portion 35 of the outer member 22.

In one non-limiting example, interference can be accomplished by forming the longitudinal protrusions 30, 31 by puncturing through the inner member 27. Puncturing of the inner member 27 is accomplished without removing any material from the inner member 27. The material is at least partially displaced by puncturing. Interference can be created when the displaced material which forms longitudinal protrusion 31 bears against the outer member 22 so as to prevent manual movement of the inner member 27 into the outer member 22. Moreover, in addition to the longitudinal protrusion 31 another longitudinal protrusion 30 can be formed in the inner member 27, interference can be created when the displaced material which forms longitudinal protrusion 30 bears against the indentation region 33 so as to prevent manual movement of the inner member 27 from the outer member 22.

In reference to the tampon applicator 20 comprising a pair of cylindrical tubular members (outer member 22 and inner member 27), it is preferred that the longitudinal protrusions 30,31 on the inner member 27 has a maximum outside diameter that is greater than the minimum inner diameter of the outer member 22. Alternatively, in a pair of tubular members in which the inner member 27 is cylindrical and the inner member 27 has a polygonal cross-section, the longitudinal protrusions 30,31 of the inner member 27 should have a maximum outside diameter that is greater than the minimum inner dimension of the inner member 27 passing through a central axis thereof. In yet another alternative embodiment, in which the inner member 27 has a rectangular cross-section and the inner member 27 is cylindrical, the maximum length of a side of the longitudinal protrusions 30,31 is greater than a corresponding chord of the circle defined by the inner diameter of the inner member 27. More preferably, the maximum outside diameter of the longitudinal protrusions 30,31 is targeted to at least equal to the inside diameter of the indentation region 33. This allows for variability inherent in manufacturing processes to ensure that interference will occur between the indentation region 33 and longitudinal protrusions 30, 31 located on the inner member 27.

The longitudinal protrusion(s) 30, 31 may encompass the entire perimeter or may encompass part of the perimeter of the inner member 27. In one non-limiting example, the longitudinal protrusions 30, 31 are spaced discontinuously around the perimeter of the inner member 27.

The longitudinal protrusions 30, 31 can be of any number, shape, or size as long as the longitudinal protrusions 30, 31 are able to engage with the indentation region 33. Any number of longitudinal protrusions 30, 31 may be utilized. In one non-limiting example, the inner member 27 may comprise two or more longitudinal protrusions 30, 31. The longitudinal protrusion(s) 30, 31 can be any shape as long as such shape would work effectively to interlock with the indentation region 33 located on the hollow interior portion 35 of the outer member 22. While longitudinal protrusion 30, 31 is shown, these could be replaced by raised areas of any desired shape provided that there is interlocking between the indentation region 33 and the longitudinal protrusions 30, 31. Longitudinal protrusion 30, 31 features may take the form of bumps, pyramids, rings, and the like. Moreover, longitudinal protrusions 30, 31 may form any pattern. In one non-limiting example, the longitudinal protrusions 30, 31 may form the pattern of two rows. Preferably, the longitudinal protrusions 30, 31 projects radially outward from the inner member 27 by at least about 0.1 mm, and more preferably, by at least about 1 mm, and most preferably, by at least about 3 mm.

The longitudinal protrusions 30, 31 can be joined to the inner member 27 or formed in the inner member 27 in any way known in the art. The longitudinal protrusions 30, 31 can also be monolithic with the inner member 27, for example, by molding the longitudinal protrusions 30, 31 and the inner member 27 as one piece. In one non-limiting example, the longitudinal protrusions 30, 31 can be joined to the outer member 22 by friction fitting that snaps parts together, gluing, and/or melting.

Longitudinal protrusions 30, 31 are typically formed inherently by the embossing process. While any conventional embossing technique can be utilized, a preferred method is to support the inner 27 member on a central mandrel having circumferential ridges in its surface, and contact the surface of the inner member 27 with a set of rolling dies having indentations corresponding in shape to the ridges on the mandrel. It is also preferred that heat be employed during the embossing process to enhance the formability of the paper.

C. Tampon Applicator Materials

Different tampon applicator parts can be constructed from different materials and processes. The tampon applicator or any part of the tampon applicator can be formed of a spirally wound, convolutedly wound, or longitudinally seamed hollow tube that is formed from paper, paperboard, cardboard, or any combinations thereof. The tampon applicator or any part of the tampon applicator can also be injection molded, extruded, or formed from flexible plastic, such as thermoformed from plastic sheet or folded or wound from plastic film.

The tampon applicator or any part of the tampon applicator can be constructed from a single ply of material or be formed from two or more plies that are bonded together to form a laminate. The use of two or more plies or layers is preferred for it enables the manufacturer to use certain materials in the various layers that can enhance the performance of the tampon applicator or any part of the tampon applicator. When two or more plies are utilized, all the plies can be spirally wound, convolutedly wound, or longitudinally seamed to form an elongated cylinder. The tampon applicator or any part of the tampon applicator can be constructed using a smooth thin ply of material on the outside or exterior surface that surrounds a coarser and possibly thicker ply. When the tampon applicator or any part of the tampon applicator contains at least three plies, the middle ply can be the thicker ply, and the interior and exterior plies can be smooth and/or slippery to facilitate the expulsion of the tampon and to facilitate the insertion of the tampon applicator or any part of the tampon applicator into a woman's vagina. By sandwiching a thick, coarser ply of material between two thin, smooth plies, a tampon applicator or any part of the tampon applicator can be provided which is very functional. The tampon applicator or any part of the tampon applicator should contain one to four plies, although more plies can be utilized if desired.

The plies forming the tampon applicator or any part of the tampon applicator can be held together by an adhesive, such as glue, heat, pressure, ultrasonic, or any combinations thereof. The adhesive can be either water-soluble or water-insoluble. A water-soluble adhesive is preferred for environmental reasons in that the tampon applicator or any part of the tampon applicator will quickly break apart when it is immersed in water. Such immersion will occur should the tampon applicator or any part of the tampon applicator be disposed of by flushing it down a toilet. Exposure of the tampon applicator or any part of the tampon applicator to a municipal's waste treatment plant wherein soaking in water, interaction with chemicals, and agitation all occur, will cause the tampon applicator or any part of the tampon applicator to break apart and evenly disperse in a relatively short period of time.

The tampon applicator is preferably constructed from 1 to 4 plys of paper, preferably three plys, and has a thickness of from about 0.127 mm to 0.559 mm, more preferably about 0.254 mm. The outer surface of the inner member 27 is preferably spaced from the inner surface of the outer member 22 by about 0.1 mm to 4 mm.

EXAMPLES

The following is a listing of examples illustrating various embodiments of the present invention. It would be obvious to those skilled in the art that various other changes and modifications can be made without departing from the spirit and scope of the invention.

Example 1

The tampon applicator of the present invention can comprise the outer member of the length of 70 millimeters, an inner member of the length of 73 millimeters, and a tampon of the length of 42 millimeters.

The outer member includes an indentation region located 10 millimeters from the gripper end along the longitudinal axis. The indentation region has a depth of 0.3 millimeters.

The inner member includes a longitudinal protrusion located 5 millimeters from the first end of the inner member along the longitudinal axis. This longitudinal protrusion has a height of 0.3 millimeters. Another longitudinal protrusion is located 3 millimeters from the second end of the inner member along the longitudinal axis. This longitudinal protrusion has height of 0.3 millimeters.

Example 2

The tampon applicator of the present invention can comprise the outer member of the length of 70 millimeters, an inner member of the length of 73 millimeters, and a tampon of the length of 50 millimeters.

The outer member includes an indentation region located 5 millimeters from the gripper end along the longitudinal axis. The indentation region has a depth of 0.5 millimeters.

The inner member includes a longitudinal protrusion located 5 millimeters from the first end of the inner member along the longitudinal axis. This longitudinal protrusion has a height of 0.5 millimeters. Another longitudinal protrusion is located 3 millimeters from the second end of the inner member along the longitudinal axis. This longitudinal protrusion has a height of 0.5 millimeters.

Example 3

The tampon applicator of the present invention can comprise the outer member of the length of 67.7 millimeters, an inner member of the length of 66.7 millimeters, and a tampon of the length of 46 millimeters.

The outer member includes an indentation region located 15 millimeters from the gripper end along the longitudinal axis. The indentation region has a depth of 0.8 millimeters.

The inner member includes a longitudinal protrusion located 5 millimeters from the first end of the inner member along the longitudinal axis. This longitudinal protrusion has a height of 0.8 millimeters. Another longitudinal protrusion is located 3 millimeters from the second end of the inner member along the longitudinal axis. This longitudinal protrusion has a height of 0.8 millimeters.

Example 4

The tampon applicator of the present invention can comprise the outer member of the length of 70 millimeters, an inner member of the length of 73 millimeters, and a tampon of the length of 48 millimeters.

The outer member includes an indentation region located 25 millimeters from the gripper end along the longitudinal axis. The indentation region has a depth of 0.7 millimeters.

The inner member includes a longitudinal protrusion located 5 millimeters from the first end of the inner member along the longitudinal axis. This longitudinal protrusion has a height of 0.7 millimeters. Another longitudinal protrusion is located 3 millimeters from the second end of the inner member along the longitudinal axis. This longitudinal protrusion has a height of 0.7 millimeters.

Example 5

The tampon applicator of the present invention can comprise the outer member of the length of 70 millimeters, an inner member of the length of 73 millimeters, and a tampon of the length of 45 millimeters.

The outer member includes an indentation region located 20 millimeters from the gripper end along the longitudinal axis. The indentation region has a depth of 0.6 millimeters.

The inner member includes a longitudinal protrusion located 5 millimeters from the first end of the inner member along the longitudinal axis. This longitudinal protrusion has a height of 0.6 millimeters. Another longitudinal protrusion is located 3 millimeters from the second end of the inner member along the longitudinal axis. This longitudinal protrusion has a height of 0.6 millimeters.

All documents cited in the Detailed Description of the Invention are incorporated, in relevant part, herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon applicator comprising:
   a) an outer member adapted to house a tampon, the outer member having an outer surface, an insertion end, and a fingergrip region comprising an indentation region that extends inwardly from the outer surface;
      i. the indentation region has a depth dimension that is measured from the outer surface of the outer member to a lowest point of the indentation region;

ii. the indentation region comprises a first raised portion and a second raised portion, each of which having a height dimension that is measured from an individual raised portion's base to an individual raised portion's highest point, wherein the height dimension is less than the depth dimension;

iii. the first raised portion being a different size and a different shape as compared to the second raised portion;

b) an inner member adapted to be received by the outer member;

c) wherein the inner member comprises a protrusion to engage the indentation region of the outer member to define an interlock so that a disassembly force required to separate the inner member from the outer member is at least 100 grams as measured by a Dillon Force Gauge.

2. The tampon applicator of claim 1, wherein the indentation region extends completely around the perimeter of the outer member.

3. The tampon applicator of claim 1, wherein the indentation region extends partially around the perimeter of the outer member.

4. The tampon applicator of claim 1, wherein the outer member and the inner member are constructed from different materials.

5. The tampon applicator of claim 1, wherein the disassembly force is at least 300 grams.

6. The tampon applicator of claim 1, wherein the depth dimension is from about 1 millimeter to about 10 millimeters.

7. The tampon applicator of claim 1, wherein the height dimension is from about 0.1 millimeter to about 10 millimeters.

8. The tampon applicator of claim 1, wherein the height dimension is from about 0.2 millimeter to about 5 millimeters.

9. The tampon applicator of claim 1, wherein the first raised portion is spaced apart from the second raised portion.

10. A tampon applicator comprising:

a) an outer member adapted to house a tampon, the outer member having an outer surface, an insertion end, and a fingergrip region comprising an indentation region that extends inwardly from the outer surface;

i. the indentation region has a depth dimension that is measured from the outer surface of the outer member to a lowest point of the indentation region;

ii. the indentation region comprises a raised portion having a height dimension that is measured from a raised portion's base to a raised portion's highest point, wherein the height dimension is less than the depth dimension;

b) an inner member adapted to be received by the outer member;

c) wherein the inner member comprises a protrusion to engage the indentation region of the outer member to define an interlock so that a disassembly force required to separate the inner member from the outer member is at least 100 grams as measured by a Dillon Force Gauge.

* * * * *